US006891612B1

(12) United States Patent
Koike et al.

(10) Patent No.: US 6,891,612 B1
(45) Date of Patent: May 10, 2005

(54) OPTICAL INSPECTION DEVICE THAT DETECTS HOLES IN AN OBJECT TO BE INSPECTED

(75) Inventors: Takashi Koike, Hamamatsu (JP); Toyoshi Ito, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/129,729

(22) PCT Filed: Nov. 11, 1999

(86) PCT No.: PCT/JP99/06281

§ 371 (c)(1),
(2), (4) Date: May 10, 2002

(87) PCT Pub. No.: WO01/35084

PCT Pub. Date: May 17, 2001

(51) Int. Cl.[7] .............................................. G01N 21/00
(52) U.S. Cl. ................. 356/237.6; 250/559.42
(58) Field of Search ................... 356/237.1–237.6, 356/429–431, 239.1; 250/559.4, 559.42, 559.43, 559.45, 559.46

(56) References Cited

U.S. PATENT DOCUMENTS

| | | | | |
|---|---|---|---|---|
| 3,710,129 A | * | 1/1973 | Gibson | 250/559.42 |
| 4,371,897 A | | 2/1983 | Kramer | 358/294 |
| 4,728,800 A | * | 3/1988 | Surka | 250/559.42 |
| 5,798,531 A | * | 8/1998 | Harris | 250/559.03 |
| 6,380,549 B1 | * | 4/2002 | Oster et al. | 250/559.42 |

FOREIGN PATENT DOCUMENTS

| | | |
|---|---|---|
| JP | 58-70134 | 4/1983 |
| JP | 4-282441 | 10/1992 |
| JP | 4-309849 | 11/1992 |
| JP | 04 309849 | 11/1992 |
| JP | 5-281156 | 10/1993 |
| JP | 9-318558 | 12/1997 |
| JP | 11-326239 | 11/1999 |
| JP | 2001249005 A | * 9/2001 |

OTHER PUBLICATIONS

M. F. Laguesse; "Optical Detection and Localization of Holes in Strips Using A Fluorescent Fiber Sensor"; IEEE Transactions on Instrumentation and Measurement, IEEE Inc., vol. 39, No. 1; Feb. 1990; pp. 242–246; XP000101446.

* cited by examiner

Primary Examiner—Hoa Q. Pham
(74) Attorney, Agent, or Firm—Morgan, Lewis & Bockius LLP

(57) ABSTRACT

An optical inspection device (1) that detects holes in an object to be inspected (11), comprising: a light source (41) that illuminates the object to be inspected by emitting illumination light from light-emitting points (41a) that are arranged in a linear or planar pattern; a fluorescent member (61), disposed on the opposite side from the light sources across the object to be inspected, having an incident surface (61A) on which the part of the illumination light emitted from the light source that passes through the holes in the object to be inspected falls incident, and a detection surface (61B) from which fluorescent light that is generated according to the incidence of the illumination light is emitted; and a photodetector (71) that detects fluorescent light that is emitted from the detection surface of the fluorescent member.

5 Claims, 5 Drawing Sheets

OPTICAL INSPECTION DEVICE THAT DETECTS HOLES IN AN OBJECT TO BE INSPECTED

TECHNICAL FIELD

The present invention relates to an optical inspection device that optically detects the presence or absence of holes in the object being inspected.

BACKGROUND ART

In the fabrication of thin films such as metal films, magnetic films, coating films, vapor deposition films, and so on, the presence of holes (through holes) has a large impact on quality, and thus it is important to inspect for the presence of holes in the thin film being inspected. In conventional optical inspection devices that detect the presence of holes in the object being inspected, a light source and a photodetector are disposed on either side of the object being inspected and an optical detector detects the light beam that passes through the holes (through holes) in the object being inspected of the light beams emitted from the light source, thereby determining, based on the output of the detector, whether or not there are holes in the item being inspected. In addition, Japanese Patent Application Laid-open No. H 5-281156 discloses an optical inspection device that illuminates the object to be inspected while scanning the light, and uses a light-focusing optical system to focus the light that passes through the object to be inspected in order to detect, using a photodetector, the light thus focused.

DISCLOSURE OF THE INVENTION

However, the conventional optical inspection device described above has had the following problems: in an inspection device wherein the holes (through holes) in the object to be inspected are detected simply by placing a light source such as a light-emitting diode opposite to a photodetector such as a photomultiplier tube and then placing the object to be inspected between the two, holes can only be detected in cases wherein the holes are on a straight line between the light source and the photodetector. Because of this, the range over which the presence or absence of holes can be confirmed is narrow, and confirming whether or not holes exist over the entire area of the object to be inspected, requires an operation to move the object to be inspected and so on.

Furthermore, in the optical inspection device disclosed in the aforementioned Japanese Patent Application Laid-open No. H 5-281156, a laser beam that is emitted from a point source was scanned, using a scanning mechanism, over the object to be inspected, such as is made clear in FIG. 1 of the application publication, and thus, on the outer edges of the object to be inspected, for example, the laser beam is incident at an angle. In such a case, if there is a through hole that has a diameter that is as large as or larger than the thickness of the film of the object to be detected or thereabouts, the laser light passes through this through hole, thereby enabling verification of the existence of the through hole; however, for through holes having diameters smaller than the thickness of the film, the laser beam is not able to pass through this through hole due to reasons such as the laser beam being blocked by the inner wall surface of the through hole, making detection of the hole portion difficult.

However, in practice objects to be detected that are in the form of thin films sometimes cannot tolerate the existence of even minute holes having diameters smaller than the film thickness. For example, in an object to be detected that has a 500 $\mu$m film thickness, it might be necessary to detect through holes with diameters of around 20 $\mu$m. Notwithstanding, it is extremely difficult to detect such through holes with very small diameters using the conventional optical inspection devices including that disclosed in Japanese Patent Application Laid-open No. H 5-281156.

The present invention was created in order to solve such conventional problems, and as such has an object of providing an optical inspection device that is able to confirm the presence of even holes with small diameters easily, all at once, and over a broad range.

The optical inspection device according to the present invention is an optical inspection device that detects holes in an object to be inspected, and comprises (1) a light source that illuminates the object to be detected by emitting illumination light from light emitting points arranged in either a linear or planar pattern, (2) a fluorescent member that is disposed on the opposite side from the aforementioned light source across the object to be detected, and that has an incident surface on which that part of the illumination light emitted from the aforementioned light source that passes through a hole in the object to be detected falls incident, and a detection surface from which a fluorescent light generated with the incidence of the illumination light is emitted, and (3) a photodetector that detects the fluorescent light that is emitted from the detection surface of the aforementioned fluorescent member.

In this optical inspection device, when there is a hole (through hole) in the object to be inspected, the part of the illumination light emitted by the light source that passes through a hole in the object to be inspected becomes incident on the incident surface of the fluorescent member after passing through the hole in the object to be inspected. In the fluorescent member, fluorescent light is generated with the incidence of the illumination light, whereupon the fluorescent light is emitted from the detection surface of the fluorescent member to fall incident on the photodetector, and is thus detected by the photodetector. In other words, the presence or absence of a hole in the object to be inspected is detected based on whether or not the fluorescent light is detected by the photodetector. Here, in the present invention, a fluorescent member is interposed between the light source and the photodetector, making it possible to confirm the presence of a hole if the light that passes through the hole becomes incident on the fluorescent member, and thus the holes that can be detected are not limited to those that exist in the straight line linking the light source and the photodetector, but rather holes can be detected over a broad area. Furthermore, in the present invention, a light source is used that has light emitting points in a linear or planar pattern, so it is possible to confirm all at once whether or not there is a hole in a broad area and, additionally, in contrast to a device wherein a laser beam emitted from a point source is scanned, the problem wherein illumination light only falls incident at an angle, such as described above, is solved, making it possible to detect holes with small diameters easily.

Furthermore, in the optical inspection device according to the present invention, a support part is provided that both supports the object to be detected and that has an aperture part through which the illumination light that is emitted from the light source can pass, where the incident surface of the fluorescent member is preferably larger than the aperture part. In this case, the fluorescent member covers the inspection area of the object to be inspected, making it possible to detect most of the illumination light that passes through the holes in the object to be inspected.

In addition, in the optical inspection device according to the present invention, it is preferable for the light source to be such that the light-emitting element is disposed in either a linear or planar pattern.

Furthermore, in the optical inspection device according to the present invention, it is preferable that a diffusion plate to be provided which illuminates the object to be inspected by diffusing the illumination light that is emitted from the light source. In this case, the presence or absence of holes is detected even when the holes in the object to be inspected are at an angle, since the illumination light diffused by the diffusion plate passes through the holes.

Furthermore, in the optical inspection device according to the present invention, it is preferable to provide a light shielding member which the illumination light is not permitted to permeate to a surface aside from the incident surface of the fluorescent member. In this case, no noise light is generated due to the incidence of external light on the fluorescent member. Furthermore, in the optical inspection device according to the present invention, it is preferable to provide a reflecting member, which reflects the fluorescent light onto surfaces aside from the detection surface of the fluorescent member. In this case, the fluorescent light that is generated in the fluorescent member efficiently falls incident on the photo detector.

BEST MODE FOR CARRYING OUT THE INVENTION

Preferable embodiments of the present invention will be described in detail below with reference to the attached drawings. Note that identical elements in the descriptions of the drawings are labeled with identical symbols, and redundant explanations have been omitted.

[First Embodiment]

Figure 1A:
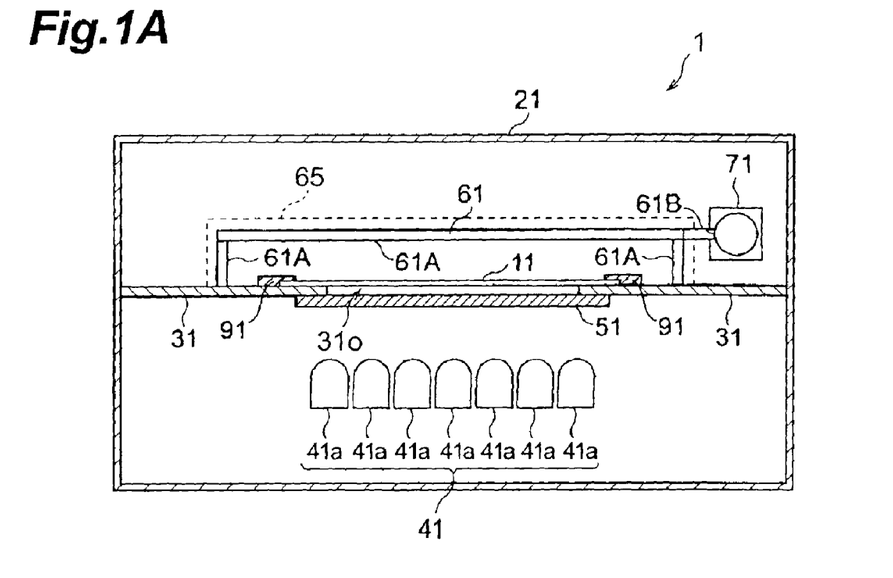
FIG. 1A is a cross-sectional drawing of a first embodiment of an optical inspection device according to the present invention.
Figure 1B:
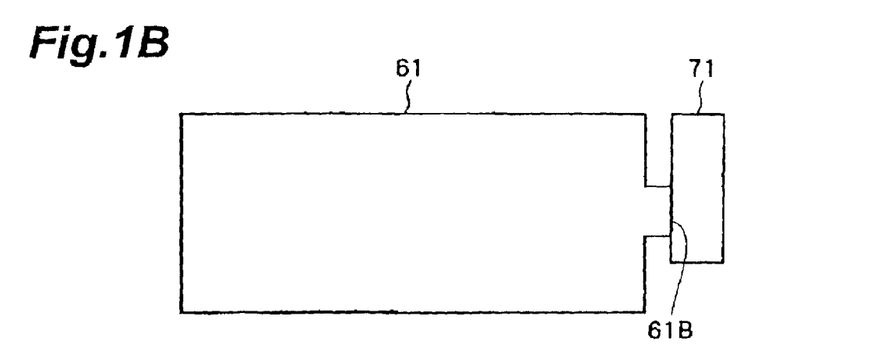
FIG. 1B is a planar view of a fluorescent plate and a photodetector in the optical inspection device shown in FIG. 1A.
Figure 1C:
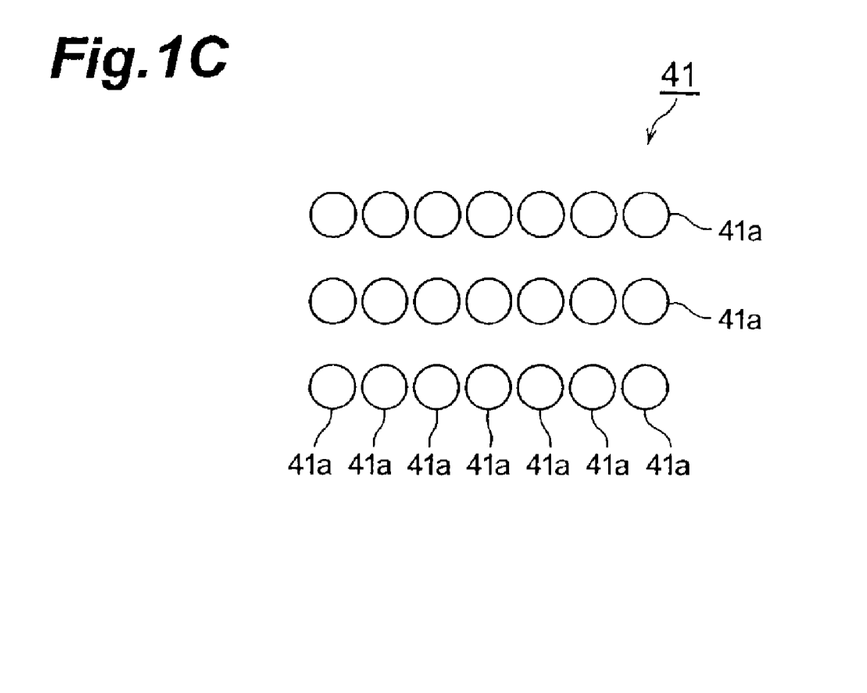
FIG. 1C is a planar view showing a light source wherein a light-emitting element is disposed in a planar pattern.
Figure 1D:
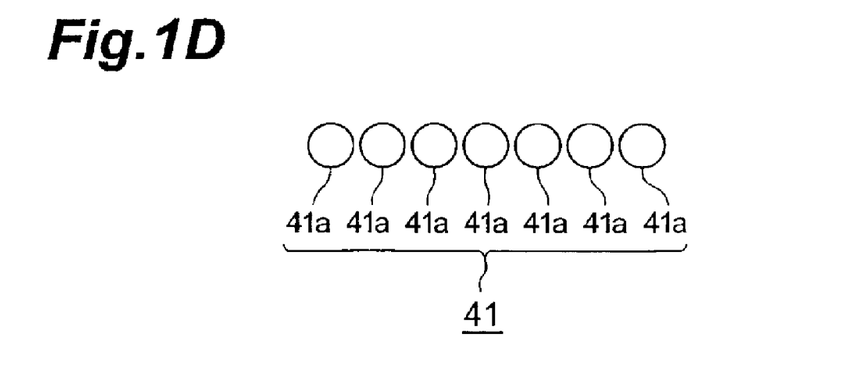
FIG. 1D is a planar view showing a light source wherein a light-emitting element is disposed in a linear pattern.

A first embodiment will be explained with reference to FIGS. 1A through 1D. An optical inspection device 1 according to the present embodiment comprises a stage (support part) 31 that supports the object to be inspected, a light source 41, a diffusion plate 51, a fluorescent plate 61, and a photodetector 71, inside a light-shielding case 21. FIG. 1A is a cross-sectional drawing of this optical inspection device, and FIG. 1B is a planar view of the fluorescent plate 61 and the photodetector 71.

The light-shielding case 21 is to prevent light from the outside from entering into the inside. The stage 31 is equipped so as to divide the inside of the light-shielding case 21 into two parts, and the outer periphery thereof is in contact with the inner wall of the light-shielding case 21, with an aperture part 31o formed in the central part thereof. An object to be inspected 11 is placed on the stage 31 so as to cover the aperture part 31o. Additionally, a mask 91 is provided to cover the edges of the object to be inspected 11 that is placed on the stage 31. This mask 91 is to prevent the passage of noise light from gaps between the stage 31 and the object to be inspected 11.

A light source 41 is provided under the aperture part 31o of the stage 31 that is on the inside of the light-shielding case 31. The illumination light emitted from the light source 41 is light of a wavelength that is able to excite the fluorescent materials that are included in the fluorescent plate 61. Additionally, a light source that has light emitting points in a linear or a planar pattern is used as the light source 41. In the present embodiment, light-emitting elements 41a, such as light-emitting diodes or semiconductor lasers, are arranged in a planar pattern such as those shown in the planar view in FIG. 1C. Conversely, as is shown in the planar view in FIG. 1D, the light-emitting elements 41a, such as light-emitting diodes or semiconductor lasers, may also be arranged in a plurality of line patterns. Also, light-emitting points in a linear pattern, as in fluorescent light and the like, may be used. In particular, it is preferable for the light-source 41 to be a surface light source wherein the light-emitting points exist in a continuous or diffused surface pattern in substantially the same shape as the aperture part 31o of the stage 31.

The diffusion plate 51 is provided above the light source 41 and beneath the aperture part 31o of the stage 31, within the light-shielding case 21. The diffusion plate 51 diffuses the illumination light that is emitted from the light source 41, whereupon the diffused illumination light shines in the direction of the object to be inspected 11 to illuminate it from all directions.

The fluorescent plate 61 is provided on top of the aperture part 31o of the stage 31 within the light-shielding case 21 so as to cover the object to be inspected 11. In addition, the incident surface 61A of the fluorescent plate 61 is broader than the aperture surface area of the aperture part 31o. The fluorescent plate 61 is, for example, a resin plate made of acrylic, vinyl, or the like, including a fluorescent material, and when there is a hole (through hole) in the object to be inspected 11, the illumination light that passes through the aforementioned hole falls incident [on the fluorescent plate 61], and the fluorescent materials are excited by the incidence of this illumination light, thus generating fluorescent light.

The fluorescent plate 61 can be a single flat plate, or, as shown in the figure, can be in the shape of a box to form a darkroom in conjunction with the stage 31 and the object to be inspected 11. When the fluorescent plate 61 is structured in a box-shape, a transparent contact adhesive, or the like, is used when adhering the flat plate, thus causing the illumination light which passes through the holes in the object to be inspected 11 and propagates in all directions to be incident on the fluorescent plate 61, making it possible to detect the fluorescent light generated accordingly, thus increasing the fluorescent light detection efficiency or, in other words, increasing hole detection efficiency.

Preferably, a light-shielding member is provided so as to prevent the passage of illumination light to surfaces aside from the incident surface 61A of the fluorescent plate 61 on which the light that passes through the holes in the object to be inspected 11 falls incident. As is shown in FIG. 1A, when the fluorescent plate 61 is structured in the shape of a box, the incident surface 61A of the fluorescent plate 61 is the inner wall surface of the box, so the light-shielding member 65 is equipped on the outer wall surface of the box. In so doing, it is possible to increase the fluorescent light detection sensitivity, or in other words, the hole detection sensitivity, because no fluorescent light which becomes noise light is generated on the incident surface 61A of the fluorescent plate 61 due to external light. Additionally, when the illumination light that is incident on the fluorescent plate 61 is reflected by the light-shielding member 65 to again propagate within the fluorescent plate 61, the proportion of the fluorescent material that is excited within the fluorescent plate 61 increases, and, in this way also, the fluorescent light detection sensitivity, or in other words, the hole detection sensitivity, is increased.

In addition, it is preferable that a reflective member that is made to reflect the fluorescent light be provided on the surface aside from the detection surface 61B of the fluorescent plate 61, which emits fluorescent light to the photodetector 71. When this is done, the fluorescent light that is generated when illumination light is incident on the fluorescent plate 61 is reflected by the reflective member, reducing the proportion that leaks to the outside of the fluorescent plate 61, and thereby increasing the hole detection efficiency due to efficient detection by the photodetector 71.

Note that the light-shielding member and reflective member may each be multiple layer films formed on the surface of the fluorescent plate 61. Additionally, the light-shielding member and the reflective member need not necessarily be separate parts. For example, a coating film or a vapor deposited film, such as aluminum, or a plate-shaped member may be used as a light-shielding member that prevents the transmission of the illumination light, and as a reflecting member that reflects fluorescent light. When the light-shielding member and the reflecting member are combined in this way, they are provided on the surfaces aside from the incident surface 61A and the detection surface 61B of the fluorescent plate 61. Note that the light-shielding member 65 in FIG. 1A also fulfills the role of the reflecting member.

The photodetector 71 detects the fluorescent light that is emitted from the detection surface 61B of the fluorescent plate 61, and can be, for example, a photomultiplier tube or a semiconductor light-receiving element (such as a photodiode). It is preferable to use a photomultiplier tube as the photodetector 71 because of its high sensitivity. Further, it is preferable to use a side-on photomuitiplier tube as the photodetector 71 because of even higher sensitivity due to high quantum efficiency over a broad light-receiving surface area.

Furthermore, when the cross-section of the fluorescent plate 60 is large in comparison with the light-receiving surface of the photodetector 71, then the size of the detection surface 61B of the fluorescent plate 60 is matched with the size of the light-receiving surface of the photodetector 71. At this time, instead of adhesing together two rectangular fluorescent plates using an adhesive, the structure of the fluorescent plate 61, as shown in FIG. 1B, can be made by, for example, cutting out a single fluorescent plate. In so doing, it is possible to eliminate the absorption of the fluorescent light by the adhesive, thereby avoiding a reduction in the detection efficiency.

The optical inspection device 1 according to the present embodiment functions as follows. The illumination light that is emitted from the light source 41 is diffused by the diffusion plate 51 and illuminates from all directions the object to be inspected 11, which is placed so as to cover the aperture part 31o on the stage 31. If there are holes (through holes) in the object to be inspected 11, then the illumination light passes through the holes to fall incident on the incident surface 61A of the florescent plate 61. In the fluorescent plate 61, fluorescent light is generated by the excitation of the fluorescent materials accompanying the incidence of the illuminated light. Then, the fluorescent light becomes incident on the light-receiving surface of the photodetector 71 after its emission from the detection surface 61B of the fluorescent plate 61, and is detected by the photodetector 71. In other words, the presence or absence of holes in the object to be inspected 11 is detected on the basis of the detection of fluorescent light by the photodetector 71.

In this way, in the optical inspection device 1 according to this embodiment, the illumination light that passes through the holes in the object to be inspected 11 is not detected directly, but rather this illumination light falls incident on the fluorescent plate 61, and the fluorescent light thus produced is detected, and thus the holes that can be detected are not limited to those that are on a direct line between the light-emitting element 41a and the photodetector 71, but rather, holes can be detected over a broad range. Additionally, in the present embodiment, a light source 41 wherein the light-emitting point is in a surface pattern is used, and thus the presence or absence of holes over a broad area can be confirmed all at once, and, additionally, in contrast to devices wherein a laser beam that is emitted from a point source is scanned, the problem with the illumination light being incident only at an angle is solved, making it possible to detect with ease even holes with small diameters.

Furthermore, the surface area of the incident surface 61A of the fluorescent plate 61 is equal to or greater than the aperture surface area of the aperture part 31o of the stage 31, and thus most of the illumination light that passes through holes that exist in the object to be inspected 11 becomes incident on the incident surface 61A. Because of this, it is possible to determine with high accuracy whether or not there are holes in the object to be inspected 11.

Furthermore, the optical inspection device 1 according to the present embodiment does not require a large optical system, and is easy to design and easy to optically adjust, making the entire equipment small and inexpensive. In addition, through the use of the diffusion plate 51, it is possible to detect with ease the presence or absence of holes even if the diameters of the holes are smaller than the film thickness of the object to be inspected 11, and even if the holes are at an angle.

Additionally, because the object to be inspected 11, the light source 41, the diffusion plate 51, the fluorescent plate 61, and the photodetector 71 are enclosed within the light-shielding case 21, no external light falls incident on the fluorescent plate 61 to cause noise light. Furthermore, when a light-shielding member is provided on surfaces aside from the incident surface 61A of the fluorescent plate 61, then, in this area also, no external light falls incident on the florescent plate 61 to cause the emission of noise light. When a reflective member is provided on a surface aside from the detection surface 61B of the fluorescent plate 61, then the fluorescent light that is generated on the fluorescent plate 61 falls incident on the light-receiving surface of the photodetector 71 efficiently. Consequently, it is possible to detect with high sensitivity whether or not there are holes in the object to be inspected 11.

[Second Embodiment]

Figure 2A:
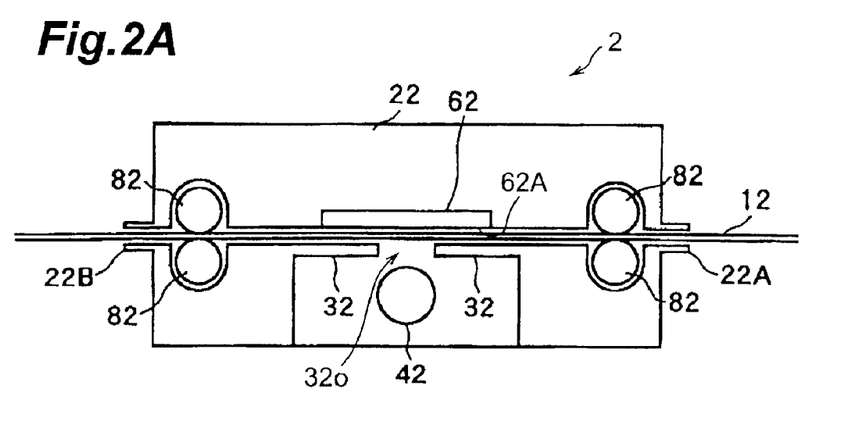
FIG. 2A is a cross-sectional drawing of a second embodiment of the optical inspection device according to the present invention.
Figure 2B:
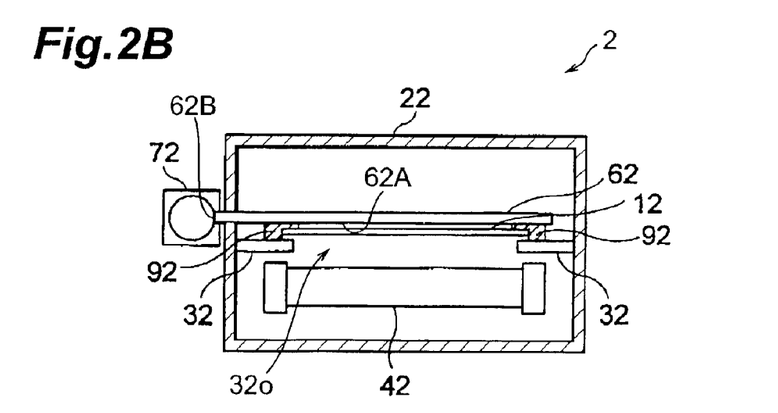
FIG. 2B is another cross-sectional of a second embodiment of the optical inspection device according to the present invention.

Next, a second embodiment will be explained with reference to FIG. 2A and FIG. 2B. An optical inspection device 2 according to the present embodiment is constituted in comprising a stage 32, a light source 42, a fluorescent plate 62, a photodetector 72, and a roller 82, in a light-shielding case 22. The optical inspection device according to the present embodiment continuously inspects an object to be inspected 12 that is in a long tape-form in one direction, such as magnetic tape, for example, while this object is in motion in this one direction. FIG. 2A is a cross-sectional diagram of the optical inspection device on the plane that is parallel to the direction of movement of the object to be inspected 12 and that is perpendicular to the direction in which the tape-shaped object to be inspected 12 extends, and FIG. 2B is a cross-sectional diagram of the optical inspection device on the plane that is perpendicular to the direction of movement of the object to be inspected 12.

A light-shielding case 22 prevents light from the outside from entering into the inside, and the tape-shaped object to be inspected 12 is introduced into the entrance 22A and delivered from the exit 22B. The entrance 22A and the exit 22B of the light-shielding case 22 are each structured so as to make it difficult for external light to enter. A stage (support part) 32 is provided so as to divide the inside of the light-shielding case 22 into two parts, and the periphery thereof is in contact with the inside walls of the light-shielding case 22, and an aperture part 32o is provided in the center area thereof. A roller 82 moves the object to be inspected 12, which has entered through the entrance 22A of the light shielding case 22, in such a way that this object to be inspected 12 covers the aperture part 32o on the stage 32 as it passes thereover, afterwards exiting from the exit 22B of the light-shielding case 22. The roller 82 also works to prevent external light from entering to the inside. Furthermore, a mask 92 is provided on the edge part of the object to be inspected 12 on the stage 32. This mask 92 is to prevent noise light from passing through gaps between the stage 32 and the object to be inspected 12.

A light source 42 is provided beneath the aperture part 32o of the stage 32. The illumination light that is emitted from the light source 42 is a light of a wavelength that is able to excite the fluorescent material included in the fluorescent plate 62. In the present embodiment, a fluorescent light wherein the light-emitting points are in a linear pattern is used as the light source 42; however, multiple semiconductor light-emitting elements arranged in a linear or a surface pattern may be used instead. Note also that "the light-emitting points are in a linear pattern" means that the light-emitting points extend in a line, and does not exclude the production of light in a radiating form from fluorescent lights and such. A diffusion plate may also be provided between the aperture part 32o of the stage 32 and the light source 42.

In the present embodiment the object to be inspected 12 is tape-shaped and moving, and thus the shape of the aperture part 32o provided in the stage 32 is preferably a slit shape that is long in the direction transverse to the object to be inspected 12. In this case, the light source 42 is preferably a linear light source that has continuous or diffused light-emitting points in a linear pattern, matching the shape of the aperture part 32o of the stage 32.

The fluorescent plate 62 is provided so as to cover the part of the object to be inspected 12 that is above the aperture part 32o of the stage 32. The fluorescent plate 62 is made of, for example, a resin plate such as acrylic or vinyl, and includes fluorescent materials so that when there is a hole in the object to be inspected 12 above the aperture part 32o of the stage 32, the illumination light that passes through the aforementioned hole falls incident on the fluorescent plate 62 and, with the incidence of this illumination light, the fluorescent materials become excited, thus producing fluorescent light. Furthermore, the incident surface 62A of the fluorescent plate 62 is made to be wider than the aperture surface area of the aperture part 32o.

As in the case of the first embodiment, in this embodiment also it is preferable to provide a light-shielding member which prevents the passage of illumination light on a surface other than the incident surface of the fluorescent plate 62 on which the illumination light that has passed through the holes in the object to be inspected 12 is incident, and also preferable to provide a reflective member, to reflect the fluorescent light, on a surface other than the detection surface of the fluorescent plate 62 which emits fluorescent light to the photodetector 72.

The photodetector 72 is for detecting the fluorescent light that is emitted from the detection surface 62B of the fluorescent plate 62 using, for example, a photomultiplier tube or a semiconductor light-receiving element. Although in the figure the photodetector 72 is outside of the light-shielding case 22, it may also be equipped within the light-shielding case 22.

The optical inspection device 2 according to the present embodiment operates as follows. The tape-shaped object to be inspected 12 is fed by the roller 82 into the light-shielding case 22 through the entrance 22A, then passes over the aperture part 32o of the stage 32 and exits the light-shielding case 22 from the exit 22B. The illumination light that is emitted from the light source 42 illuminates the part of the object to be inspected 12 that is over the aperture part 32o of the stage 32. When there is a hole (through hole) in the part of the object to be inspected 12 that is illuminated by the illumination light, the illumination light passes through this hole to fall incident on the incident surface 62A of the fluorescent plate 62. In the fluorescent plate 62, the fluorescent material is excited by the incidence of the illumination light, thus producing fluorescent light. Then, this fluorescent light is emitted from the detection surface of the fluorescent plate 62 to fall incident on the light-receiving surface of the photodetector 72, and is detected by the photodetector 72. In other words, the detection of the presence or absence of holes in the part of the object to be inspected 12 which is illuminated by the illumination light is based on whether or not fluorescent light is detected by the photodetector 72.

In this way, the illumination light that passes through a hole in the object to be inspected 12 is not detected directly in the optical inspection device 2 according to the present embodiment either, but instead the illumination light falls incident on the fluorescent plate 62 and the fluorescent light that is thus produced is detected, making it possible to detect holes over a broad area rather than limiting the holes that can be detected to those that are on the direct line connecting the light source 42 to the photodetector 72. Furthermore, in the present embodiment, a light source 42 wherein the light-emitting points are in a linear pattern is used, thus making it possible to verify all at once whether or not there are holes in a broad area, and moreover, in contrast to devices wherein a laser beam that is emitted from a point source is scanned, the problem with the illumination light being incident only at an angle is solved, making it possible to detect with ease even holes with small diameters.

Furthermore, because the surface area of the incident surface 62A of the fluorescent plate 62 is greater than the aperture area of the aperture part 32o of the stage 32, most of the illumination light that passes through the holes in the object to be inspected 12 falls incident on the incident surface 62A. Because of this, it is possible to judge with high accuracy whether or not there are holes in the object to be inspected 12.

Furthermore, the optical inspection device 2 according to this embodiment also does not require a large optical system, and is easy to design and easy to optically adjust, making the entire equipment small and inexpensive. In addition, through the use of the diffusion plate, it is possible to detect with ease the presence or absence of holes even if the diameters of the holes are smaller than the film thickness of the object to be inspected 12, and even if the holes are at an angle.

Additionally, the part of the object to be inspected 12 that is illuminated by the illumination light, the light source 42, and the fluorescent plate 62 are all enclosed in the light-shielding case 22, so no external light falls incident on the fluorescent plate 62 to cause noise light. Furthermore, when a light-shielding member is provided on a surface aside from the incident surface of the fluorescent plate 62, here also, no external light falls incident on the fluorescent plate 62 to cause noise light. When a reflective member is provided on a surface aside from the detection surface of the fluorescent plate 62, the fluorescent light that is generated on the fluorescent plate 62 becomes incident on the light-receiving surface of the photodetector 72 efficiently. Consequently, it becomes possible to detect with high sensitivity whether or not there are holes in the object to be inspected 12.

Furthermore, in the optical inspection device 2 according to the present embodiment, the inspection is performed while the tape-shaped object to be inspected 12 is moved in the lengthwise direction, so it is possible to detect whether or not there are holes in the object to be inspected 12 along the longitudinal direction, and it is also possible to detect the position of the holes in the longitudinal direction of the object to be detected 12.

[Third Embodiment]

Figure 3:
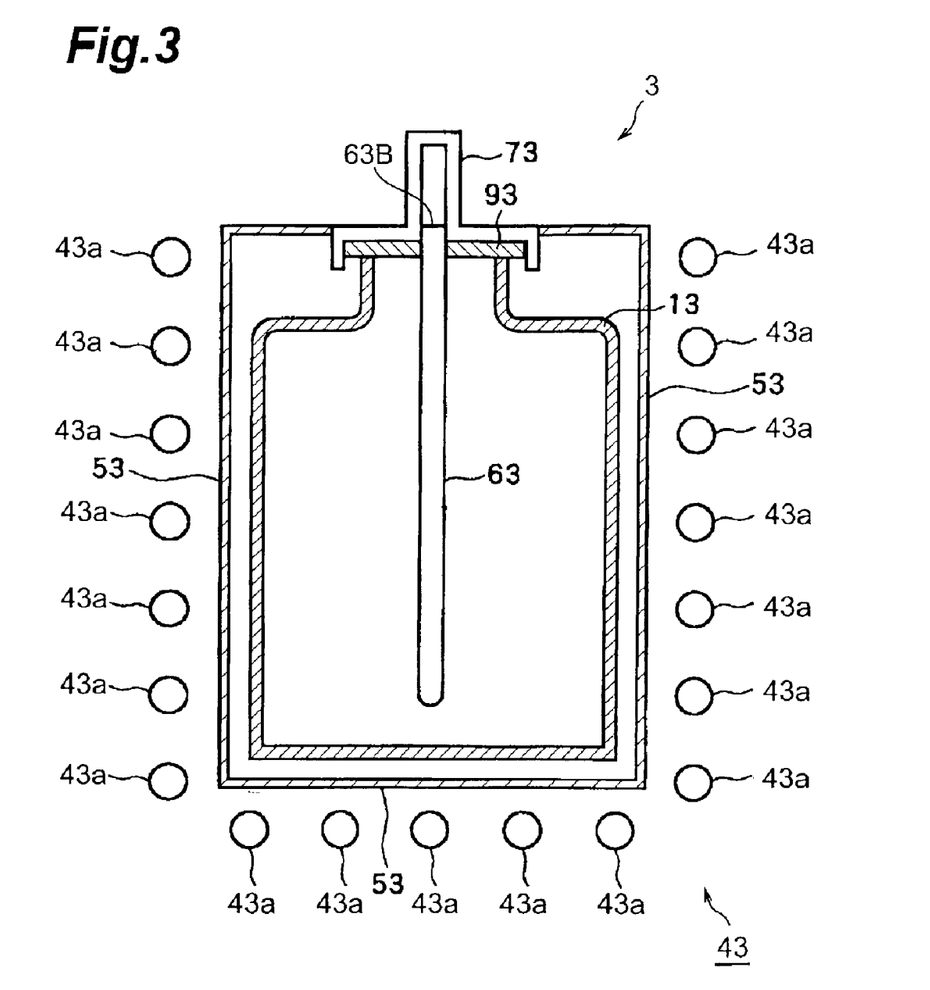
FIG. 3 is a structural drawing of a third embodiment of the optical inspection device according to the present invention.

A third embodiment will now be explained. FIG. 3 is a structural diagram of an optical inspection device 3 according to the third embodiment. The optical inspection device according to this embodiment is constituted in comprising a light source 43, a diffusion plate 53, a fluorescent tube 63, and a photodetector 73. The object to be inspected 13 in this embodiment is a container such as a metal tank or can, or is a coating layer or a vapor deposition layer on the inside wall of a container.

The light source 43 is provided so as to surround the object to be inspected 13 in order to illuminate the entire outside wall of the object to be inspected 13 with illumination light. The illumination light that is emitted from the light source 43 is light of a wavelength that can excite the fluorescent materials included in the fluorescent tube 63. The light source 43 in the present embodiment can be structured by arranging a plurality of semiconductor light-emitting devices 43a in a surface pattern; conversely, the plurality of semiconductor light-emitting elements 43a can also be arranged in a line, or a fluorescent light or the like may also be used. A diffusion plate 53 is provided between the object to be inspected 13 and the light source 43. The diffusion plate 53 diffuses the illumination light that is emitted from the light source 43 so that this diffused illumination light illuminates the entire outside wall of the object to be inspected 43 from all different directions.

The fluorescent tube 63 is inserted into the interior of the object to be inspected 13 through an opening therein. The fluorescent tube 63 is, for example, a resin tube of acrylic, vinyl, or the like, including fluorescent materials, and when there is a hole in the object to be inspected 13, the illumination light that passes through this hole falls incident on [the fluorescent tube 63] so that the fluorescent materials are excited by the incidence of the illumination light and therefore emit fluorescent light.

Preferably, a reflecting member that reflects the fluorescent light is provided on a surface aside from the detection surface of the fluorescent tube 63 that emits fluorescent light to the photodetector 73. In so doing, the fluorescent light which is generated after illumination light falls incident on the reflection tube 63 is reflected by the reflecting member so that the proportion of the fluorescent light leaked to the outside is reduced, thereby improving the hole detection efficiency through efficient detection by the photodetector 73.

The photodetector 73 detects the fluorescent light that is emitted from the detection surface 63B of the fluorescent tube 63, and uses, for example, a photomultiplier tube or a semiconductor light-receiving element. As is shown in the figure, the detection surface 63B of the fluorescent tube 63, and the photodetector 73 are provided either in the vicinity of or outside of the opening of the item to be detected 13, and thus packing 93 is provided at the opening of the object to be inspected 13 so that external light does not enter into the inside of the object to be inspected 13.

The optical inspection device 3 according to the present embodiment operates as follows. The illumination light emitted from the light source 43 is diffused by the diffusion plate 53 and illuminates from all directions the entire outside wall of the object to be inspected 13. If there is a hole (through hole) in the object to be inspected 13, the illumination light passes through this hole and falls incident on the incident surface of the fluorescent tube 63. In the fluorescent tube 63 the fluorescent materials are excited by the incidence of the illumination light, producing fluorescent light. This fluorescent light is emitted from the detection surface of the fluorescent tube 63 to fall incident on the light-receiving surface of the photodetector 73, and is detected by the photodetector 73. In other words, the presence or absence of holes in the object to be inspected 13 is detected based on whether or not fluorescent light is detected by the photodetector 73.

In this way, the illumination light that passes through the holes in the object to be inspected 13 is not detected directly in the optical inspection device 3 according to this embodiment either, but rather the fluorescent light that is generated when the illumination light falls incident on the fluorescent tube 63 is detected, and thus holes can be detected over a broad range rather than limiting the holes that can be detected to those that are on the straight line linking the optical element 43A to the photodetector 73. Additionally, in the present embodiment a light source 43 that has light-emitting points in a surface pattern is used, and thus it is possible to verify all at once whether or not there are holes over a broad range and, furthermore, in contrast to devices wherein a laser beam emitted from a point source is scanned, the problem with the illumination light only becoming incident at an angle is solved, making it possible to detect even holes with small diameters with ease.

Furthermore, in the optical inspection device 3 according to the present embodiment, a large optical system is not needed and the design and optical adjustment thereof are easy, making the entire device small and inexpensive. In addition, the use of the diffusion plate 53 makes it possible to detect the presence or absence of holes with ease, even when the holes have diameters that are smaller than the thickness of the film in the object to be inspected 13, and even when the holes are at an angle.

[Fourth Embodiment]

Figure 4:
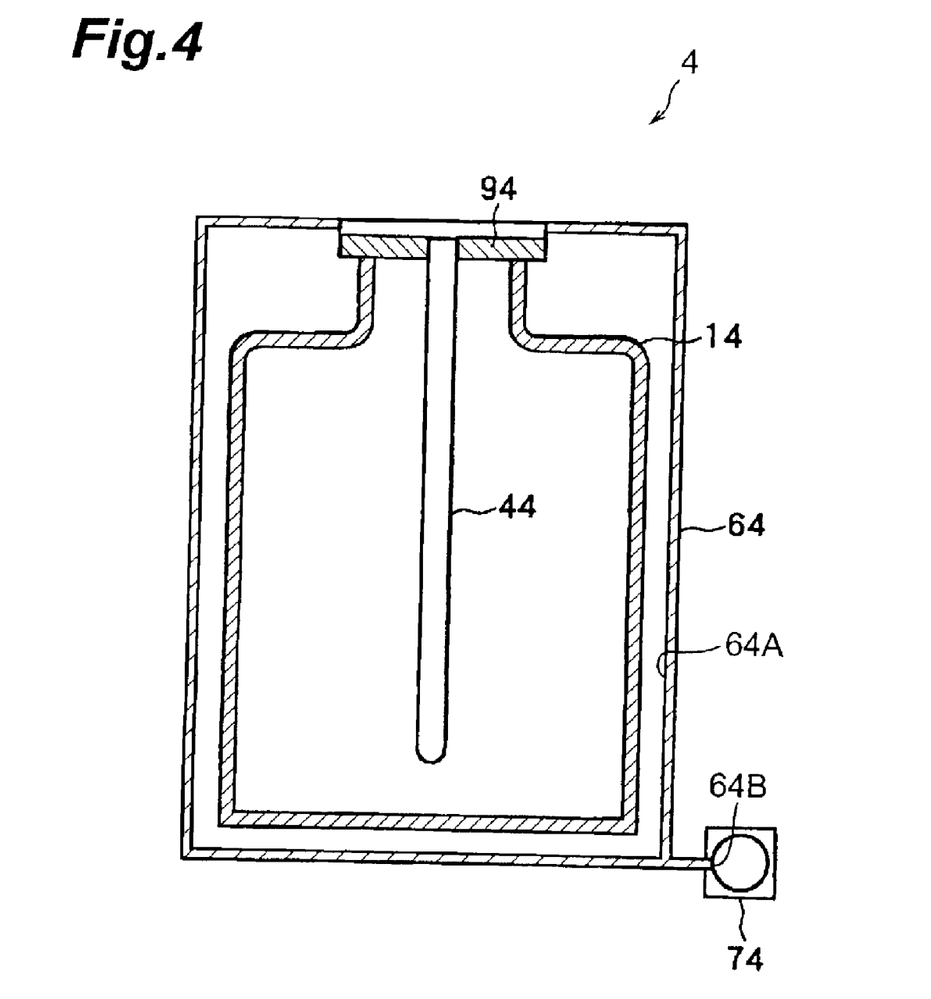
FIG. 4 is a structural drawing of a fourth embodiment of the optical inspection device according to the present invention.

A fourth embodiment will now be explained. FIG. 4 is a structural diagram of an optical inspection device 4 according to a fourth embodiment. The optical inspection device 4 according to this embodiment is constituted in comprising a light source 44, a fluorescent plate 64, and a photodetector 74. The object to be inspected 14 in this embodiment, similarly to that of the third embodiment, is a container such as a metal tank or can, or a coating layer or vapor deposition layer on the wall surface of the container.

A light source 44 is provided in the interior of the object to be inspected 14 so as to illuminate the entire inner wall of the object to be inspected 14 with illumination light. The illumination light that is emitted from the light source 44 is a light with a wavelength that can excite the fluorescent materials that are contained in a fluorescent plate 64. Additionally, in this embodiment, a fluorescent light wherein light-emitting points are in a linear pattern is used as the light source 44; otherwise, a plurality of semiconductor light-emitting elements arranged in a linear or surface pattern may also be used. Note also that "light-emitting points are in a linear pattern" means that the light-emitting points extend along a straight line, and does not exclude the production of light in a radiating form from fluorescent lights and such. As is shown in the figure, the light source 44 is inserted from the opening in the object to be inspected 14, and thus packing 94 is provided in the opening of the object to be inspected 14 so as to prevent external light from entering into the interior of the object to be inspected 14. A diffusion plate may be provided around the light source 44 inside the object to be inspected 14.

The fluorescent plate 64 is disposed so as to surround the outer periphery of the object to be inspected 14. This fluorescent plate 64 is, for example, a resin plate made from acrylic or vinyl, and includes fluorescent materials. If there is a hole (through hole) in the object to be inspected 14, then the illumination light that passes through this hole falls incident on [the fluorescent plate 64], where the fluorescent materials are excited by the incident illumination light, causing the production of fluorescent light.

As in the first embodiment, it is preferable in this embodiment also that a light-shielding member be provided on a surface other than the incident surface of the fluorescent plate 64 wherein the illumination light that passes through the holes in the object to be inspected 14 is incident, that is, on the outside wall surface, to prevent the entry of illumination light, and further preferable that a reflecting member be provided on a surface other than the detection surface of the fluorescent plate 64 that emits fluorescent light to the photodetector 74, to reflect the fluorescent light.

The photodetector 74 detects the fluorescent light that is emitted from the detection surface 64B of the fluorescent plate 64, and uses, for example, a photomultiplier tube or a semiconductor light-receiving element.

The optical inspection device 4 according to the present embodiment operates as follows. The illumination light that is emitted from the light source 44 illuminates the entire inner wall of the object to be inspected 14. If there is a hole in the object to be inspected 14, the illumination light passes through this hole to fall incident on the incident surface 64A of the fluorescent plate 64. In the fluorescent plate 64 the fluorescent materials are excited by the incidence of the illumination light and produce fluorescent light. Then, this fluorescent light is emitted from the detection surface 64B of the fluorescent plate 64 to fall incident on the light-receiving surface of the photodetector 74 and is detected by the photodetector 74. In other words, the detection of the presence or absence of holes in the object to be inspected 14 is based on whether or not fluorescent light is detected by the photodetector 74.

In this way, the illumination light that passes through the holes in the object to be inspected 14 is not detected directly in the optical inspection device 14 according to this embodiment either, but rather the illumination light falls incident on the fluorescent plate 64 and the fluorescent light thus produced is detected, and thus it becomes possible to detect holes over a broad range rather than limiting the holes that can be detected only those holes that lie on a direct line linking the light source 44 and the photodetector 74. Also in this embodiment, by using a light source 44 in which the light-emitting points exist in a linear pattern, it is possible to confirm all at once whether or not there are holes over a broad range, and additionally, in contrast to devices in which a laser beam emitted from a point source is scanned, the problem with the illumination light only being incident at an angle is solved, enabling easy detection even of those holes with small diameters.

Furthermore, the optical inspection device according to the present embodiment does not require a large optical system, and is easy in terms of design and optical adjustment, making the overall device small and inexpensive. Furthermore, through the use of a diffusion plate, it is possible to detect the presence or absence of holes with ease, even when the diameter of the holes is smaller than the thickness of the film on the object to be inspected 14, and even if the holes are at an angle.

INDUSTRIAL APPLICABILITY

As is explained above, the optical inspection device according to the present invention does not directly detect the illumination light that passes through holes in the object to be inspected, but rather detects the fluorescent light that is produced by the incidence of this illumination light on a fluorescent plate, and thus the holes that can be detected are not limited to only those that are on the direct line linking the light source and the photodetector, but rather it becomes possible to detect holes over a broad range. Additionally, because a light source is used wherein the location of light-emission assumes a linear pattern, it is possible to confirm all at once whether or not there are holes in a broad range. Furthermore, in contrast to devices wherein a laser beam that is emitted from a point source is scanned, the problem with the illumination light being incident at an angle is solved, enabling easy detection of even those holes that have small diameters.

What is claimed is:

1. An optical inspection device that detects holes in an object to be inspected, comprising:

a light source that emits an illumination light from light-emitting points in a linear or planar pattern in order to illuminate said object to be inspected;

a fluorescent member that is disposed on the opposite side from light sources across said object to be inspected, and has an incident surface on which the portion of the illumination light that is emitted from said light source that passes through holes in said object to be inspected falls incident, and a detection surface from which fluorescent light that is generated with the incidence of said illumination light is emitted; and a photodetector that detects the fluorescent light that is emitted from said detection surface of said fluorescent member;

wherein a light-shielding member that does not allow the passage of said illumination light is provided on a surface other than said incident surface of said fluorescent member.

2. An optical inspection device according to claim 1, wherein a support part is provided which supports said object to be inspected, and which also has an aperture part through which the illumination light that is emitted by said light source can pass; and wherein said incident surface of said fluorescent member is wider than said aperture part.

3. An optical inspection device according to claim 1, wherein said light source has light-emitting elements that are arranged in either a linear or planar pattern.

4. An optical inspection device according to claim 1, further comprising a diffusion plate that diffuses the illumination light emitted from said light source to illuminate said object to be inspected.

5. An optical inspection device according to claim 1, wherein a reflective member that reflects said fluorescent light is provided on a surface other than said detection surface of said fluorescent member.

* * * * *